US010675479B2

(12) United States Patent
Yasumuro et al.

(10) Patent No.: US 10,675,479 B2
(45) Date of Patent: Jun. 9, 2020

(54) OPERATION TEACHING DEVICE AND TRANSCRANIAL MAGNETIC STIMULATION DEVICE

(71) Applicants: OSAKA UNIVERSITY, Suita-shi, Osaka (JP); A SCHOOL CORPORATION KANSAI UNIVERSITY, Suita-shi, Osaka (JP); TEIJIN PHARMA LIMITED, Tokyo (JP)

(72) Inventors: Yoshihiro Yasumuro, Suita (JP); Ryo Ebisuwaki, Settsu (JP); Youichi Saitoh, Ikeda (JP); Taiga Matsuzaki, Tokyo (JP)

(73) Assignees: OSAKA UNIVERSITY, Osaka (JP); A SCHOOL CORPORATION KANSAI UNIVERSITY, Osaka (JP); Teijin Pharma Limited, Tokyo (JP)

( * ) Notice: Subject to any disclaimer, the term of this patent is extended or adjusted under 35 U.S.C. 154(b) by 652 days.

(21) Appl. No.: 15/107,303

(22) PCT Filed: Jun. 30, 2014

(86) PCT No.: PCT/JP2014/067432
§ 371 (c)(1),
(2) Date: Dec. 22, 2016

(87) PCT Pub. No.: WO2015/098155
PCT Pub. Date: Jul. 2, 2015

(65) Prior Publication Data
US 2017/0128737 A1 May 11, 2017

(30) Foreign Application Priority Data
Dec. 24, 2013 (JP) ................................ 2013-265132

(51) Int. Cl.
A61N 2/00 (2006.01)
A61B 5/00 (2006.01)
(Continued)

(52) U.S. Cl.
CPC ............ A61N 2/006 (2013.01); A61B 5/1077 (2013.01); A61B 5/1079 (2013.01);
(Continued)

(58) Field of Classification Search
CPC ............ G06T 19/006; G06T 11/00–80; G06K 9/00362–00389; G06K 9/00335–00355; G06K 2009/00395
See application file for complete search history.

(56) References Cited

U.S. PATENT DOCUMENTS

2003/0073899 A1 4/2003 Ruohonen et al.
2004/0039279 A1 2/2004 Ruohonen
(Continued)

FOREIGN PATENT DOCUMENTS

JP 2003-180649 A 7/2003
JP 2004-636 A 1/2004
(Continued)

OTHER PUBLICATIONS

International Search Report dated Aug. 12, 2014 from the International Bureau in counterpart International Application No. PCT/JP2014/067432.
(Continued)

Primary Examiner — Daniel F Hajnik
(74) Attorney, Agent, or Firm — Sughrue Mion, PLLC

(57) ABSTRACT

An operation teaching device used in operation teaching during movement and/or rotation operation of an object (2h) to adjust the object to a predetermined position and direction, including: a TOF type depth image camera (40) for obtaining three-dimensional shape information about the
(Continued)

object; extraction means for extracting a feature region from the three-dimensional shape information acquired by the TOF type depth image camera (40) using a luminance image of the object obtained from information about light receiving intensity of the projection light, the projection light being reflected from the object and received with light receiving means; and generation means for generating information for the operation teaching by calculating a deviation between the three-dimensional shape information including the feature region of the object in the predetermined position and direction and the three-dimensional shape information including the feature region of the object in a current position and direction.

10 Claims, 10 Drawing Sheets

(51) Int. Cl.
*A61N 2/02* (2006.01)
*G06K 9/00* (2006.01)
*G01S 17/89* (2020.01)
*G06K 9/20* (2006.01)
*G06T 7/73* (2017.01)
*A61B 5/107* (2006.01)
*G09B 23/28* (2006.01)

(52) U.S. Cl.
CPC ............ *A61B 5/6803* (2013.01); *A61N 2/008* (2013.01); *A61N 2/02* (2013.01); *G01S 17/89* (2013.01); *G06K 9/00201* (2013.01); *G06K 9/00255* (2013.01); *G06K 9/00362* (2013.01); *G06K 9/209* (2013.01); *G06T 7/74* (2017.01); *G09B 23/28* (2013.01); *G06K 9/00268* (2013.01); *G06K 2209/05* (2013.01); *G06T 2207/10028* (2013.01); *G06T 2207/30016* (2013.01); *G06T 2207/30201* (2013.01); *G06T 2207/30244* (2013.01)

(56) References Cited

U.S. PATENT DOCUMENTS

| | | |
|---|---|---|
| 2009/0187062 A1 | 7/2009 | Saitoh |
| 2012/0206452 A1* | 8/2012 | Geisner ................ G02B 27/017 345/419 |
| 2013/0345491 A1 | 12/2013 | Saitoh et al. |
| 2014/0139340 A1* | 5/2014 | Yang ..................... G09B 19/003 340/573.1 |
| 2014/0343351 A1 | 11/2014 | Tojo et al. |
| 2015/0206003 A1* | 7/2015 | Haker ................ G06K 9/00369 345/420 |
| 2016/0030762 A1* | 2/2016 | Glass ..................... A61N 2/008 600/13 |

FOREIGN PATENT DOCUMENTS

| | | |
|---|---|---|
| WO | 2007/123147 A1 | 11/2007 |
| WO | 2012/121341 A1 | 9/2012 |
| WO | 2013/054004 A1 | 4/2013 |
| WO | 2013062021 A1 | 5/2013 |

OTHER PUBLICATIONS

International Preliminary Report on Patentability dated Jul. 7, 2016 from the International Bureau in counterpart International Application No. PCT/JP2014/067432.

P. J. Besl, et.al. "A Method for Registration of 3-D Shapes", IEEE Trans. Pattern Anal. Machine Intell, vol. 14, No. 2, pp. 239-256 (Feb. 1992).

Yoshihiro Yasumuro, et.al. "Coil Positioning System for Repetitive Transcranial Magnetic Stimulation Treatment by ToF Camera Ego-Motion" 35th Annual International Conference of the IEEE EMBS, Osaka, Japan, Jul. 3-7, 2013, pp. 3586-3589.

Yoshihiro Yasumuro, et.al. "A Technique to Support Positioning for Transcranial Magnetic Stimulation in Pain Treatment" The 13th Proceeding of the Annual Meeting of Japanese Journal for Medical Virtual Virtual Reality, Aug. 31, 2013, (3 pages total).

* cited by examiner

<POINT GROUP AND DISTANCE>

<CORRESPONDING POINT IN ICP ALGORITHM>

OPERATION TEACHING DEVICE AND TRANSCRANIAL MAGNETIC STIMULATION DEVICE

TECHNICAL FIELD

The present invention relates to an operation teaching device and a transcranial magnetic stimulation device in which the operation teaching device is used.

BACKGROUND ART

In recent years, interest is growing in a transcranial magnetic stimulation therapy as a treatment method for many patients with nervous diseases in which drug treatment is not always effective. The transcranial magnetic stimulation therapy is a relatively new treatment method for providing treatment and/or relieving a symptom by applying magnetic stimulation to a specific region (for example, an intracerebral nerve) of a brain with a magnetic field generator disposed on a scalp surface of the patient. Unlike the conventional electric stimulation method which requires craniotomy and an indwelling electrode to which a patient feels a strong resistance, the transcranial magnetic stimulation therapy is expected to become widespread as the non-invasive treatment method with a less burden on the patient.

In a specific technique of the transcranial magnetic stimulation therapy, passage of current through a coil located near the scalp surface of the patient locally generates a minute pulse magnetic field to cause eddy current in a cranium by using the principle of electromagnetic induction, thereby providing stimulation to the intracerebral nerve immediately below the coil (for example, see Patent Document 1).

According to Patent Document 1, a refractory neuropathic pain is effectively reduced by the transcranial magnetic stimulation treatment performed by the above method and a high pain reducing effect is obtained by precise local stimulation. However, it is also revealed that an optimum stimulation region slightly differs depending on an individual patient.

Accordingly, in order to obtain the high effect of the transcranial magnetic stimulation therapy, it is necessary to specify, for each patient, the optimum stimulation region of a patient's head, namely, it is necessary to correctly perform three-dimensional positioning of the treatment coil with respect to the patient's head. It is also known that the obtained effect may differ depending on an orientation (posture) of the treatment coil even if the treatment coil is located at an identical position.

As to the positioning of the treatment coil, it is known that the treatment coil is positioned with respect to the patient's head with an optical tracking system in which an infrared beam is used (for example, see Patent Documents 2 and 3). Some systems are already commercially available and used in a clinical application.

As described above, in order to obtain the pain reducing effect by the transcranial magnetic stimulation therapy, it is necessary to specify the optimum stimulation region of the patient's head to correctly provide the stimulus to the intracerebral nerve. It is difficult to know the correct position of the brain existing in the cranium from the outside. However, the position of the brain can correctly be know using three-dimensional information about a head MRI image (Magnetic Resonance Imaging). While referring to the cranial three-dimensional information obtained by the MRI image, an operator (such as a doctor) of the transcranial magnetic stimulation therapy can guide the treatment coil to the optimum stimulation region of the patient's head to correctly provide the magnetic stimulation using a positioning function of the optical tracking system.

Conventionally, in the case where the optical tracking system is used in the transcranial magnetic stimulation therapy, infrared reflective markers are installed in a fixed position associated with the patient's head (for example, a bed on which the patient lies) and the treatment coil, a current position of the treatment coil is estimated from a positional relationship between the two obtained by detection of the markers, and the treatment coil is guided to the optimum stimulation region of the patient's head while the cranial three-dimensional information obtained by the MRI image is referred to. Accordingly, the correct positioning is required between the patient's head and the MRI image. An eye, an ear, a nose, or the like is designated using a calibration marker while the patient's head is fixed to the bed, whereby the patient's head is correctly positioned with respect to the MRI image.

PRIOR ART DOCUMENTS

Patent Documents

Patent Document 1: WO 2007/123147 A
Patent Document 2: JP 2003-180649 A
Patent Document 3: JP 2004-000636 A

SUMMARY OF THE INVENTION

Problems to be Solved by the Invention

However, in the conventional method, the correct positioning between the patient's head and the MRI image is lost when the patient changes the head position and/or the posture after the calibration. Accordingly, the patient is not allowed to move while the patient's head is restricted by being fixed to the bed until the magnetic stimulation treatment ends after the calibration. This has been a large burden on the patient.

In Patent Document 1, when the transcranial magnetic stimulation therapy is performed, the pain reducing effect lasts for several hours but does not last for several days or more. Therefore, it is desirable that the transcranial magnetic stimulation therapy is performed at short time intervals, hopefully every day, from the viewpoint of the pain reducing effect. In order to provide consecutive treatment without enforcing various excessively physical and temporal burdens on the patient, it is ideal to enable the treatment at home or at a nearby family doctor's office.

However, it is assumed that the conventional transcranial magnetic stimulation device including the coil positioning device or system is generally used in a relatively large hospital or research institute where a skillful medical specialist is present. Therefore, handling and operation of the device are complicated and skill is required to use the device. It is generally difficult for the patient, a patient's family, or a nearby family doctor who is not always an expert to operate the transcranial magnetic stimulation device to provide the treatment.

Accordingly, for each time of the treatment, it is necessary that the patient, who receives the transcranial magnetic stimulation treatment, attend or be admitted to the large hospital where there is a skillful medical specialist, and the large burden is enforced on the patient in various aspects in order to repeatedly have the consecutive treatment.

The present invention has been made in view of such circumstances, and a basic object thereof is to provide an operation teaching device in which the handling and operation are simplified while the burden on the patient caused by the head restriction is reduced during the transcranial magnetic stimulation therapy, and a transcranial magnetic stimulation device in which the operation teaching device is used.

Means for Solving the Problems

An operation teaching device according to a first aspect of the present invention is used in operation teaching during movement and/or rotation operation of an object in order to adjust the object to a predetermined position and direction, the operation teaching device including: (a) time-of-flight (TOF) type depth image camera means for obtaining three-dimensional shape information about the object from information about a propagation distance of projection light from light emitting means to light receiving means through reflection on the object in each pixel of a photographed image obtained by irradiating a surface of the object with the projection light; (b) extraction means for extracting a feature region from the three-dimensional shape information using a luminance image of the object obtained from information about light receiving intensity of the projection light, the projection light being reflected from the object and received with the light receiving means; and (c) generation means for generating information for the operation teaching by calculating a deviation between the three-dimensional shape information including the feature region of the object in the predetermined position and direction and the three-dimensional shape information including the feature region of the object in a current position and direction.

An operation teaching device according to a second aspect of the present invention includes: (a) time-of-flight (TOF) type depth image camera means configured to enable movement and/or rotation operation of an object and to obtain three-dimensional shape information about the object from information about a propagation distance of projection light from light emitting means to light receiving means through reflection on the object in each pixel of a photographed image obtained by irradiating a surface of the object with the projection light; and (b) generation means for generating (1) a first index and (2) a second index based on (A) the three-dimensional shape information about the object located in a predetermined position and direction relative to the depth image camera and (B) the three-dimensional shape information about the object located in a current position and direction relative to the depth image camera, (1) the first index indicating a predetermined relative position and direction, (2) the second index indicating the current relative position and direction, a display mode of the second index being brought close to a display mode of the first index when operation to relatively move one of the object and the depth image camera is performed such that one of the object and the depth image camera is brought close to the predetermined relative position and direction.

A transcranial magnetic stimulation device according to a third aspect of the present invention is for applying magnetic stimulation to a specific region in a subject's head using magnetic field generation means located outside the head, the transcranial magnetic stimulation device including: (a) time-of-flight (TOF) type depth image camera means that is provided to be movably and/or rotatably integral with the magnetic field generation means, the TOF type depth image camera means for obtaining three-dimensional shape information about the subject's head from information about a propagation distance of projection light from light emitting means to light receiving means through reflection on a surface of the subject's head in each pixel of a photographed image obtained by irradiating a surface of the subject's head with the projection light; (b) extraction means for extracting a feature region from the three-dimensional shape information using a luminance image of the subject's head obtained from information about light receiving intensity of the projection light, the projection light being reflected from the surface of the subject's head and received with the light receiving means; and (c) generation means for generating teaching information for operation to change relative positions and directions of the magnetic field generation means and the subject's head by calculating a deviation between the three-dimensional shape information including the feature region of the subject's head in a position and direction in which the magnetic stimulation is provided to the specific region and the three-dimensional shape information including the feature region of the subject's head in a current position and direction.

In this case, the feature region is preferably a nose area or an ear area of the subject.

Further, a transcranial magnetic stimulation device according to a fourth aspect of the present invention is for applying magnetic stimulation to a specific region in a subject's head using magnetic field generation means located outside the head, the transcranial magnetic stimulation device including: (a) time-of-flight (TOF) type depth image camera means provided to be movably and/or rotatably integral with the magnetic field generation means to obtain three-dimensional shape information about the subject's head from information about a propagation distance of projection light from light emitting means to light receiving means through reflection on a surface of the subject's head in each pixel of a photographed image obtained by irradiating a surface of the subject's head with the projection light; and (b) generation means for generating (1) a first index and (2) a second index based on (A) the three-dimensional shape information about the subject's head when the magnetic field generation means is located in a position and direction in which the magnetic stimulation is provided to the specific region and (B) the three-dimensional shape information about the subject's head when the magnetic field generation means is located in a current position and direction, (1) the first index indicating a target position and direction when the magnetic field generation means provides the magnetic stimulation to the specific region, (2) the second index indicating the current position and direction when the magnetic field generation means is located in the current position and direction, a display mode of the second index being brought close to a display mode of the first index when operation to move the magnetic field generation means is performed such that the magnetic field generation means is brought close to the position and direction in which the magnetic stimulation is provided to the specific region.

Effects of the Invention

In the operation teaching device according to the first aspect of the present invention, the three-dimensional shape information about the object can be obtained in real time using the TOF type depth image camera means, and the feature region can be extracted from the three-dimensional shape information by including the extraction means. The operation teaching device of the first aspect includes the generation means, which allows the information for the operation teaching to be generated by calculating the deviation between the three-dimensional shape information including the feature region of the object in the predetermined position and direction and the three-dimensional shape information including the feature region of the object in the current position and direction.

Accordingly, even if the object deviates from the predetermined position and direction when the movement and/or rotation operation is performed on the object in order to adjust the object to the predetermined position and direction, the object can be easily and reliably adjusted to the predetermined position and direction only by the simple operation to move and/or rotate the object according to the information for the operation teaching. The deviation of the three-dimensional shape information including the feature region extracted with the extraction means is calculated, so that the information for the operation teaching can be obtained at a relatively high speed.

In the operation teaching device according to the second aspect of the present invention, the use of the TOF type depth image camera means can obtain the three-dimensional shape information about the object in real time. The operation teaching device of the second aspect includes the generation means, which allows an operator to intuitively know which direction the object of the movement operation is moved, from the display of the first and second indexes, thereby facilitating the operation.

In the transcranial magnetic stimulation device according to the third aspect of the present invention, the use of the TOF type depth image camera means can obtain the three-dimensional shape information about the subject's head in real time. In this case, because the TOF type depth image camera means and the magnetic field generation means are integrally movable and/or rotatable, a relative relationship between the TOF type depth image camera means and the magnetic field generation means is always constant with respect to the position and direction, and it is not necessary to adjust the position and direction again. The transcranial magnetic stimulation device of the third aspect includes the extraction means, which allows the feature region to be extracted from the three-dimensional shape information about the subject's head. The transcranial magnetic stimulation device of the third aspect includes the generation means, which allows the teaching information for the operation to change the relative positions and directions of the magnetic field generation means and the subject's head to be generated by calculating the deviation between the three-dimensional shape information including the feature region of the subject's head in the position and direction in which the magnetic stimulation is provided to the specific region in the subject's head and the three-dimensional shape information including the feature region of the subject's head in the current position and direction.

Accordingly, even if the magnetic field generation means deviates from the relative position and direction corresponding to the specific region of the subject's head when the relative movement and/or rotation operation between the magnetic field generation means and the subject's head is performed in order to guide the magnetic field generation means located outside the head to the position and direction corresponding to the specific region in the subject's head, the magnetic field generation means can be easily and reliably adjusted to the relative position and direction corresponding to the specific region of the subject's head only by the simple operation to relatively move and/or rotate the magnetic field generation means and the subject's head according to the information for the operation teaching. Therefore, the burden on the subject caused by the head restriction can be reduced during the transcranial magnetic stimulation therapy. The deviation of the three-dimensional shape information including the feature region extracted with the extraction means is calculated, so that the information for the operation teaching can be obtained at a relatively high speed.

As described above, a user of the device can perform the necessary operation without any conventional special skill only by relatively moving and/or rotating the magnetic field generation means and the subject's head according to the information for the operation teaching. Even the subject, the subject's family, or the nearby family doctor who is not always the expert can relatively easily operate and use the device. Because the conventional large-scale, expensive device is not required, cost can be reduced, and an installation space can easily be ensured in the subject's home or in the relatively small doctor's office and clinic. As described above, the present invention can provide the compact and inexpensive magnetic stimulation device in which the handling and operation are simplified, which allows the subject to consecutively and repeatedly receive the transcranial magnetic stimulation therapy every day at home or at the nearby family doctor's office.

In this case, the feature region to be extracted from the three-dimensional shape information about the subject's head is set to the subject's nose area or ear area. Therefore, the particularly feature region can be extracted from the face shape of the subject's head to enhance the accuracy of the deviation calculation with the generation means.

In the transcranial magnetic stimulation device according to the fourth aspect of the present invention, the use of the TOF type depth image camera means can obtain the three-dimensional shape information about the subject's head in real time. In this case, because the TOF type depth image camera means and the magnetic field generation means are integrally movable and/or rotatable, a relative relationship between the TOF type depth image camera means and the magnetic field generation means is always constant with respect to the position and direction, and it is not necessary to adjust the position and direction again. The transcranial magnetic stimulation device of the fourth aspect includes the generation means, which allows the operator to intuitively know which direction to move the movement operation object such as the subject's head or the TOF type depth image camera means from the display of the first index and the second index. Therefore, the operation is facilitated, and an obstacle is reduced when the transcranial magnetic stimulation device is used to provide the treatment at home or a medical practitioner outpatient.

Accordingly, even if the magnetic field generation means deviates from the relative position and direction corresponding to the specific region of the subject's head when the relative movement and/or rotation operation between the magnetic field generation means and the subject's head is performed in order to guide the magnetic field generation means located outside the head to the position and direction corresponding to the specific region in the subject's head, the magnetic field generation means can be easily and reliably adjusted to the relative position and direction corresponding to the specific region of the subject's head only by the simple operation to relatively move and/or rotate the magnetic field generation means and the subject's head according to the display of the first index and the second index. Therefore, the burden on the subject caused by the head restriction can be reduced during the transcranial magnetic stimulation therapy.

As described above, the user of the device can perform the necessary operation without any conventional special skill only by relatively moving and/or rotating the magnetic field generation means and the subject's head according to the display of the first index and the second index. Even the subject, the subject's family, or the nearby family doctor who is not always the expert can relatively easily operate the transcranial magnetic stimulation device. Because the conventional large-scale, expensive device is not required, cost can be reduced, and an installation space can easily be ensured in the subject's home or in the relatively small doctor's office and clinic. As described above, the present invention can provide the compact and inexpensive magnetic stimulation device in which the handling and operation are simplified, which allows the subject to consecutively and repeatedly receive the transcranial magnetic stimulation therapy every day at home or at the nearby family doctor's office.

EMBODIMENT OF THE INVENTION

Hereinafter, an embodiment of the present invention will be described with reference to the accompanying drawings by taking the case of a transcranial magnetic stimulation therapy for example. An image data processing device of the present invention can effectively be used to the case where various disease treatment magnetic stimulation therapies are provided to regions except for a head of a subject (for example, a patient or an examinee).

[Outline of Configuration of Transcranial Magnetic Stimulation Device]

Figure 1:
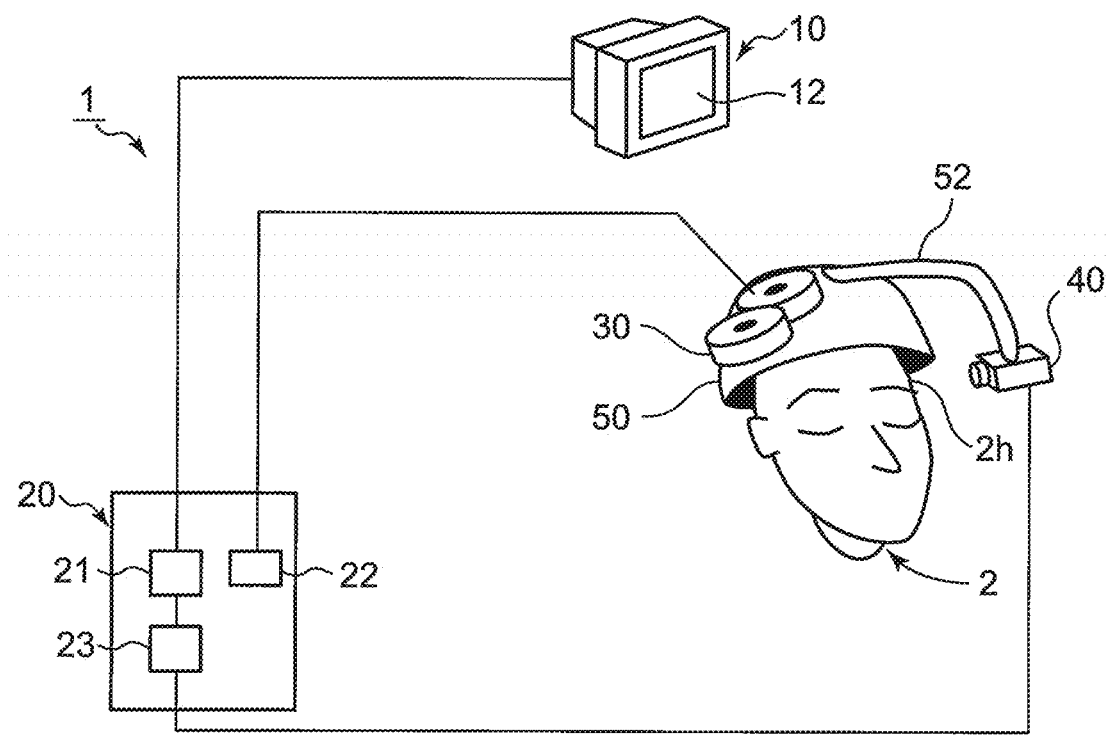
FIG. 1 is a schematic configuration diagram of a transcranial magnetic stimulation device according to an embodiment of the present invention.

FIG. 1 is an explanatory view schematically illustrating an outline of a configuration of a transcranial magnetic stimulation device according to this embodiment. The transcranial magnetic stimulation device 1 is used to provide treatment by applying magnetic stimulation to a specific region (optimum stimulation region) in a head $2h$ of a subject 2.

As illustrated in FIG. 1, the transcranial magnetic stimulation device 1 (hereinafter, simply referred to as a "device" as appropriate) includes, as main components, an image monitor 10, a device body unit 20, a magnetic stimulation coil 30 (hereinafter, referred to as a "treatment coil" or simply referred to as a "coil" as appropriate), a TOF camera 40, and a helmet 50.

The TOF camera 40 is a time-of-flight (TOF) type depth image camera, and three-dimensional shape information about an object can be obtained from information about a projection light propagation distance from light emitting means to light receiving means through reflection on an object surface in each pixel of a photographed image obtained by irradiating the object surface with projection light. In short, the TOF camera 40 is a camera that can acquire in real time a distance to all the objects in a visual field, namely, a surface shape of the object in the visual field of the camera by measuring the time until the projection light returns after being reflected from the object, and the measured surface shape data is output as point cloud data.

For example, MESA Imaging in Zurich, Switzerland has introduced a device having a product name "SR4000" to market. In the device, a subject which is the measurement object is photographed with imaging means in which a solid-state imaging element such as a CCD is used, and when the light projected to the subject from the projection means is reflected and arrives at each pixel of the solid-state imaging element, time until arrival at the pixel since the projection is detected by an optical phase difference between the projection light and pixel arriving light, thereby calculating the distance of a subject point in which an image is formed in each pixel of an imaging screen.

By using the TOF camera 40, the three-dimensional shape of the object surface can be measured in real time even at a close distance. At the same time as the three-dimensional shape of the object surface is obtained in real time, the reflection luminance image can be also obtained in real time from information about light receiving intensity of the projection light, which is reflected from the object surface and received with the light receiving means.

In this embodiment, the TOF camera 40 is fixed to one end of a holding arm 52 having predetermined strength and rigidity, and the other end of the holding arm 52 is fixed to the helmet 50. That is, the TOF camera 40 is integrally fixed to the helmet 50 via the holding arm 52. The magnetic stimulation coil 30 is also fixed to a predetermined portion of a surface of the helmet 50. Accordingly, the magnetic stimulation coil 30 and the TOF camera 40 move integrally when the helmet 50 moves, and a relative relationship between the magnetic stimulation coil 30 and the TOF camera 40 is always kept constant in the position and direction.

When the subject 2 puts the helmet 50 on the head 2h, the relative relationship between the optimum stimulation region of the subject's head 2h and the magnetic stimulation coil 30 (that is, the TOF camera 40) is fixed in the position and direction according to a mounting condition (that is, a mounting posture of the helmet 50 with respect to the head 2h). Accordingly, the subject 2 adjusts the mounting condition of the helmet 50, the relative position and direction of the magnetic stimulation coil 30 (TOF camera 40) can be adjusted with respect to the optimum stimulation region of the subject's head 2h.

The face shape of the subject 2 is measured with the TOF camera 40 in the state where the subject 2 puts on the helmet 50, which allows the relative relationship between the TOF camera 40 and the face of the subject 2 to be estimated in the position and direction from the measured face shape. The relative relationship in the position and direction represents the mounting posture of the helmet 50 on the subject 2. As described above, the magnetic stimulation coil 30 is fixed to the specific position of the helmet 50, and the relative relationship between the magnetic stimulation coil 30 and the TOF camera 40 is kept constant in the position and direction. Therefore, in the helmet 50, the mounting posture in which the positions and directions of the TOF camera 40 and the face of the subject 2 are obtained when the magnetic stimulation coil 30 stimulates the correct region (optimum stimulation region) of the brain of the subject 2 is referred to as a "correct posture", and this "correct posture" is recorded.

After the subject 2 puts on the helmet 50 again, the current mounting posture of the helmet 50, which represents the relative relationship between the TOF camera 40 and the face of the subject 2 in the position and direction, is measured as a "current posture". As described later, a distance between the "correct posture" and the "current posture" is calculated, and when the distance exceeds a prescribed range, an instruction of the direction that should be changed with respect to the relative relationship between the TOF camera 40 and the face of the subject 2 in the position and direction is issued on a monitor screen 12 of the image monitor 10 without providing the magnetic stimulation treatment. According to the instruction on the monitor screen 12, the subject 2 adjusts the mounting condition of the helmet 50, changes the relative relationship between the TOF camera 40 and the face of the subject 2 in the position and direction, and measures the "current posture" again. The operation is repeatedly performed until the distance between the "correct posture" and the "current posture" falls within the prescribed range, which allows the magnetic stimulation coil 30 to be guided to the correct position.

The image monitor 10 includes the monitor screen 12 such as a CRT screen and a liquid crystal display screen, and has a function of displaying image information. An image display of a personal computer may be used. As described above, when the distance between the "correct posture" and the "current posture" exceeds the prescribed range, the direction that should be changed with respect to the relative relationship between the TOF camera 40 and the face of the subject 2 in the position and posture is displayed on the monitor screen 12 of the image monitor 10. While viewing the display on the monitor screen 12, the operator (not illustrated) of the magnetic stimulation treatment adjusts the relative relationship between the TOF camera 40 and the face of the subject 2 in the position and posture such that the distance between the "correct posture" and the "current posture" falls within the prescribed range. Then the operator properly gives the magnetic stimulation treatment.

The device body unit 20 integrally has the following configurations or separately has a part of the following configurations, and the configurations include the following. For convenience, each configuration is divided into a plurality of configurations. In implementing the present invention, each configuration may be implemented as execution software installed on the personal computer.

Based on input from a teaching information generator 23, an image display controller 21 included in the device body unit 20 performs display control on various images to be displayed on the image monitor 10. A magnetic stimulation coil controller 22 performs on-off control of a magnetic flux generating current applied to the magnetic stimulation coil 30 and control of the magnetic flux generating current.

In the state where the magnetic stimulation coil 30 is properly brought close to the optimum stimulation region of the subject's head 2h, an operating unit (not illustrated) is operated to activate the magnetic stimulation coil controller 22. Therefore, the magnetic flux having predetermined intensity is applied to generate an induced current in the brain of the subject's head 2h, and the magnetic stimulation treatment can be provided to apply the magnetic stimulation to the optimum stimulation region.

Positioning data based on previously-acquired face shape data in the "correct posture" is readably stored in the teaching information generator 23. The positioning data is described later. The face shape data in the "correct posture" and the positioning data based on the face shape data may be readably stored in a memory device, which is provided in the teaching information controller 23 or outside the device body unit 20.

The face shape data in the "current posture" is input to the teaching information generator 23 from the TOF camera 40, and the positioning data is acquired based on the face shape data in the "current posture". The teaching information generator 23 performs the positioning of the positioning data in the "current posture" with respect to the positioning data in the "correct posture" to calculate the distance between the "correct posture" and the "current posture". When the distance exceeds the prescribed range, the teaching information for teaching the direction that should be changed with respect to the relative relationship between the TOF camera 40 and the face of the subject 2 in the position and direction is generated such that the distance between the "correct posture" and the "current posture" falls within the prescribed range, and teaching information data is output to the image monitor 10.

Each of the image display controller 21, the magnetic stimulation coil controller 22, and the teaching information generator 23 includes necessary control circuit and calculation circuit. Alternatively, as described above, the control of the device may be implemented as the execution software installed on the personal computer. In this case, the device performs necessary control and calculation for the control (to be described later) using a programmed computer or a computer that reads and executes a program recorded in a recording medium. At least a part of the program that performs the necessary control and calculation for the control using the computer and pieces of data necessary for the control and calculation is stored in an external server communicably connected to the device, and the necessary program and pieces of data are downloaded as necessary in response to a demand from the device side, which allows the necessary control and the calculation to be performed using the computer.

Basic operation of the transcranial magnetic stimulation device 1 including the configuration in FIG. 1 will specifically be described below. Because data processing procedure and method such as a specific method for calculating image processing are mainly described below, the function or operation of each configuration of the device 1 in FIG. 1 may not be directly described. However, even in such cases, because the function or operation that is described is implemented as the function or operation of the transcranial magnetic stimulation device 1 in FIG. 1, the function or operation corresponding to the configuration of the device 1 can easily be specified.

Figure 2:
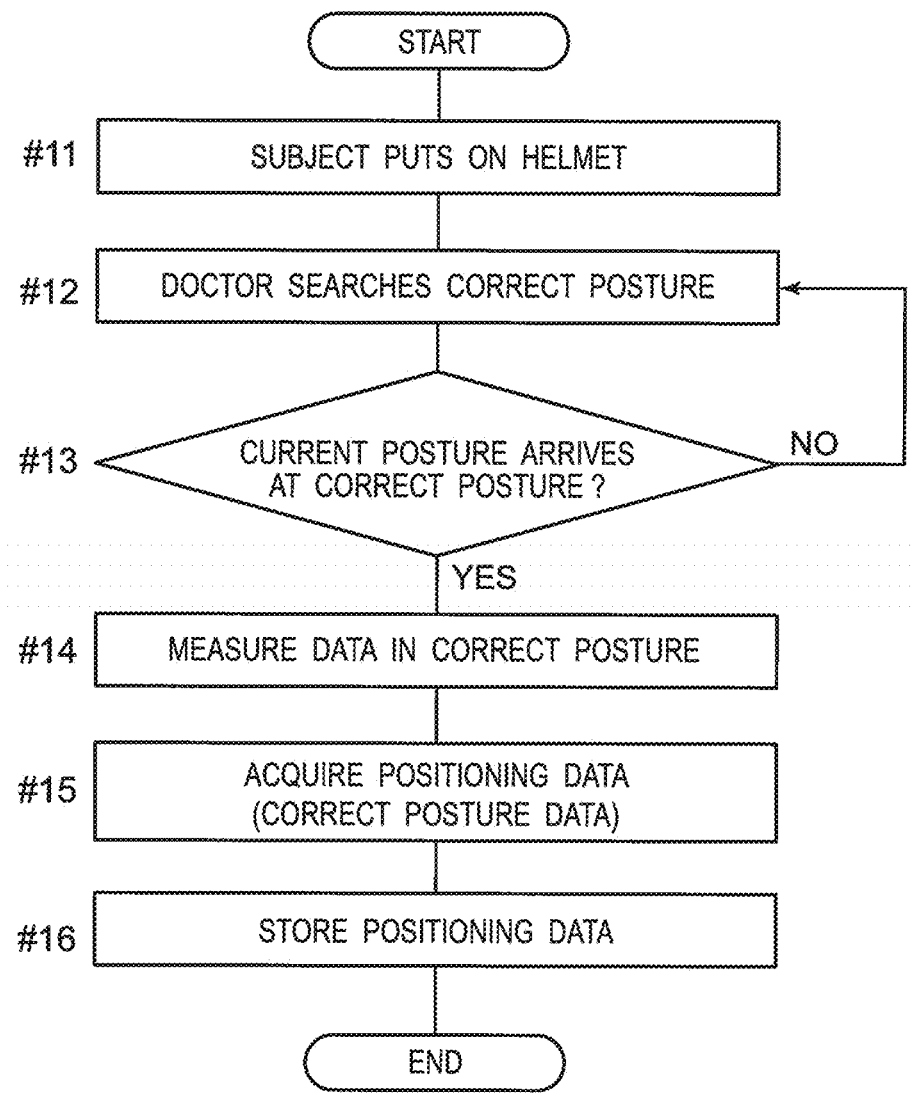
FIG. 2 is a flowchart illustrating a process of acquiring a positioning data in a "correct posture" before magnetic stimulation treatment is performed by the device in FIG. 1.

Prior to the magnetic stimulation treatment, it is necessary to measure the face shape data with respect to the "correct posture" corresponding to the position and direction of the TOF camera 40 and the face of the subject 2 when the magnetic stimulation coil 30 stimulates the optimum stimulation region of the subject's head 2*h*, acquire the positioning data based on the measured data, and record the measured data. FIG. 2 is a flowchart illustrating a process of acquiring the positioning data in the "correct posture". For example, the process is preferably performed during initial medical care performed by a special doctor in a hospital.

When the activation of the system is started, the subject 2 puts on the helmet 50 in Step #11, the doctor searches the "correct posture" while viewing the mounting condition of the helmet 50 of the subject 2 or referring to a reaction of the subject 2 in the area where the subject 2 feels a desensitization effect (or a stimulation effect) in Step #12, and whether the relative positions and directions of the TOF camera 40 and the face of the subject 2 arrive at the "correct posture" is determined (Step #13).

When the relative positions and directions arrive at the "correct posture" and the determination result is YES in Step #13, the TOF camera 40 is activated through the teaching information generator 23 by trigger input from the doctor (not-illustrated switch: ON), and the face shape data at that time (that is, in the "correct posture") is measured (Step #14).

Figure 4:
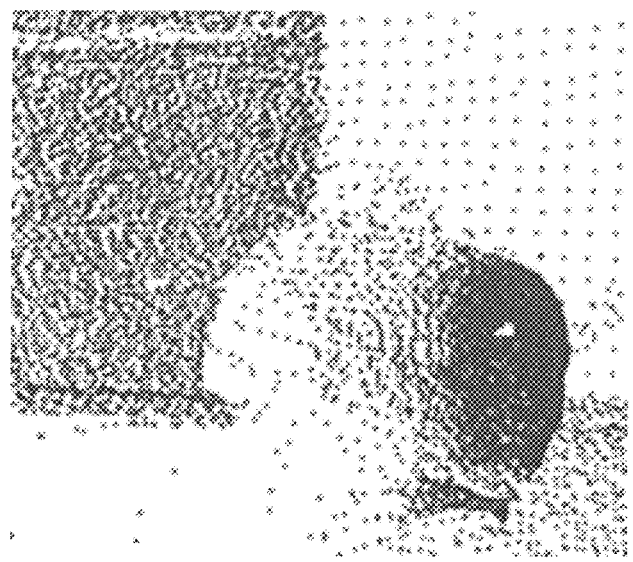
FIG. 4 is a view illustrating an example of surface shape data measured with a TOF camera included in the device in FIG. 1.
Figure 5:
FIG. 5 is a view illustrating an example of face shape data extracted from the surface shape data in FIG. 4.

As described above, the TOF camera is a camera that can measure the surface shape data of the object in the visual field in real time. For example, the measured surface shape data is output as the point cloud data as illustrated in FIG. 4. The obtained point cloud data includes data such as a background other than a target or a noise. For this reason, the noise is removed by masking in which distance information and reliability information about camera sensitivity are used and data time average. For example, as illustrated in FIG. 5, the data including only the face shape can be extracted through the pieces of processing.

The positioning data is acquired for the purpose of the positioning with respect to the "current posture" based on the measured face shape data in the "correct posture" (Step #15). In this embodiment, a difference between the "correct posture" and the "current posture" is obtained by the positioning in which an ICP algorithm (as described later, a technique of obtaining a rigid body conversion parameter by an iterative calculation so as to minimize a distance between corresponding points) is used. However, in the case where the face shape data acquired in Step #14 is directly used, calculation requires time because of a large number of data, and therefore it easily falls into a false local solution because of excessively wide shape range.

Figure 6:
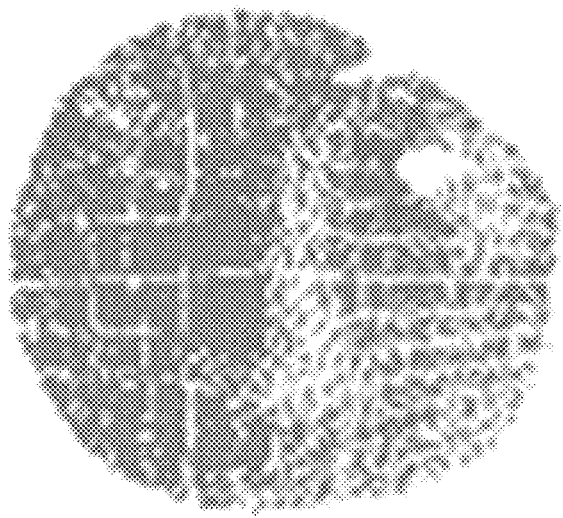
FIG. 6 is a view illustrating an example of the positioning data in the "correct posture", which is extracted from the face shape data in FIG. 5.

In order to solve the problem, a nose that is an especially feature region in the face and a surrounding area of the nose (hereinafter referred to as a "nose area") are set to the feature region, only the shape data of the nose area that is the feature region is extracted from the face shape data obtained in Step #14, and the extracted shape data of the nose area is acquired as the positioning data in the "correct posture". FIG. 6 illustrates an example of the positioning data. Alternatively, an ear that is also a feature region and a surrounding area of the ear (hereinafter referred to as an "ear area") may be set to the feature region. The obtained positioning data in the "correct posture" is stored in the teaching information controller 23, a memory device provided in the teaching information controller 23, or a memory device provided outside the device body unit 20 (Step #16), and the process of acquiring the positioning data in the "correct posture" is ended.

In this embodiment, when only the shape data of the nose area is extracted from the face shape data the subject 2, the shape data of the nose area is automatically extracted using a face recognition function obtained by implementing OpenCV that is an image processing library.

Figure 8:
FIG. 8 is a view illustrating a nose area detected by performing face recognition processing on a reflection luminance image obtained with the TOF camera included in the device in FIG. 1.
Figure 9:
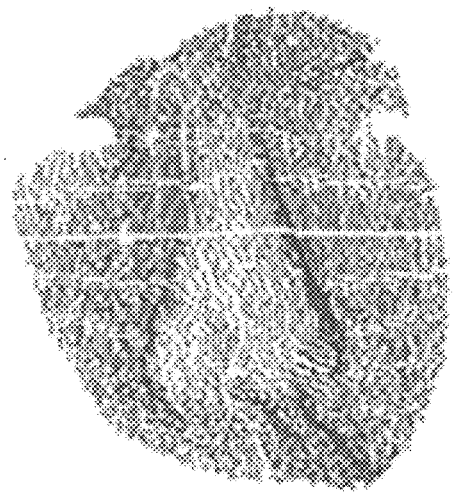
FIG. 9 is a view illustrating point cloud data obtained by extracting only a nose surrounding area in FIG. 8.

The TOF camera 40 can obtain a monochrome reflection luminance image in real time while obtaining the three-dimensional surface shape in real time. The nose area can be detected as illustrated in FIG. 8 by performing the face recognition processing on the reflection luminance image. Then, processing of extracting only an area surrounded by a circle in FIG. 8 is performed on a face shape point group in FIG. 5, and point cloud data in which only the nose surrounding area is extracted can be obtained as illustrated in FIG. 9.

<ICP (Iterative Closest Point) Algorithm>

In this embodiment, as described above, the difference between the "correct posture" and the "current posture" is obtained by the positioning in which the ICP algorithm is used. An outline of the ICP algorithm will be described below.

The ICP algorithm is a technique proposed by Besl et al. in 1992 (P. J. Besl and N. D. McKay: "A Method for Registration of 3-D Shapes", IEEE Trans. Pattern Anal. Machine Intell, vol. 14, No. 2, pp. 239-256 (1992-2)). It is a technique of obtaining the rigid body conversion parameter so as to minimize the distance between the corresponding points by the repetitive calculation. According to the technique, the point groups in which the correspondence is unknown can accurately be matched with each other.

In this embodiment, the ICP algorithm is implemented using a function of software library VTK (Visualization Tool Kit), and the following rotation matrix R and translation vector t are obtained as a rigid body conversion parameter by executing the ICP algorithm.

Using this ICP algorithm, the positioning of a nose area shape point group measured at a time point of the "correct posture" is performed with respect to a nose area shape point group measured in the "current posture", thereby calculating the difference (deviation) between the "correct posture" and the "current posture". As a result, conversion parameters (rigid body conversion parameter) of the translation vector t and the rotation matrix R can be obtained. The translation vector t and the rotation matrix R represent how much distance and in which direction the point group in the "current posture" is moved so as to match with the point group in the "correct posture".

The rigid body conversion parameter obtained herein represents how much the "current posture" and the "correct posture" are deviated from each other. Therefore, in order to bring the "current posture" close to the "correct posture", the direction to be changed is calculated from the obtained rigid body conversion parameter with respect to the relative relationship between the TOF camera 40 and the face of the subject 2 in the position and direction, and displayed on the monitor screen 12 of the image monitor 10 as illustrated in FIG. 10, for example.

Figure 10:
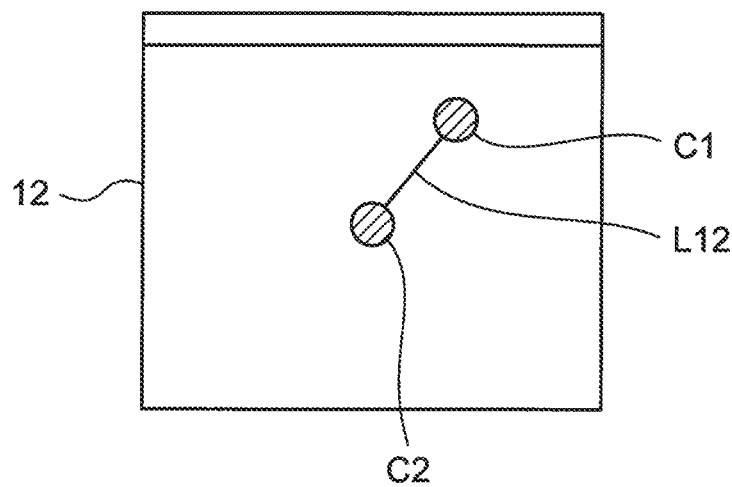
FIG. 10 is a view illustrating an example of teaching information displayed on an image monitor of the device in FIG. 1.

In the example of FIG. 10, for example, a red circle C1 corresponds to the TOF camera 40, a green circle C2 corresponds to the face (feature region) of the subject 2, and the direction of a line segment L12 connecting the circles C1 and C2 indicates the direction in which the circles C1 and C2 should be moved. Accordingly, the relative relationship (that is, the mounting posture of the helmet 50) between the TOF camera 40 and the face of the subject 2 needs to be changed in the position and direction such that the line segment L12 in the monitor screen 12 is shortened and such that the two circles C1 and C2 finally overlap each other.

A Euclidean distance d between two points $r_1$ and $r_2$ in a three-dimensional space is given by the following equation (Mathematical formula 1).

$$d(r_1, r_2) = \underset{\vec{r_1}=(x_1,y_1,z_1),\ \vec{r_2}=(x_2,y_2,z_2)}{\sqrt{(x_1-x_2)^2 + (y_1-y_2)^2 + (z_1-z_2)^2}} \quad \text{[Mathematical formula 1]}$$

Figure 12:
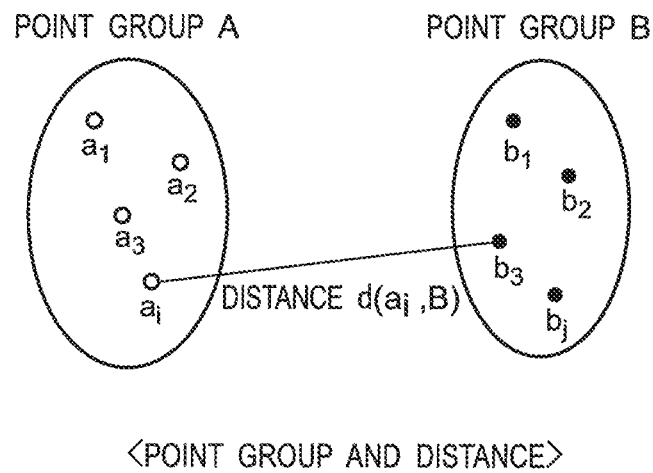
FIG. 12 is a schematic diagram illustrating a positioning method in which an ICP algorithm is used.

Here, it is assumed that two point groups, i.e., a point group A including N points $a_i$ and a point group B including M points $b_j$ exist (see (Mathematical formula 2) and FIG. 12).

$$A = \vec{a}_i, i=1,2,\ldots N$$

$$B = \vec{b}_j, j=1,2,\ldots M \quad \text{[Mathematical formula 2]}$$

Figure 13:
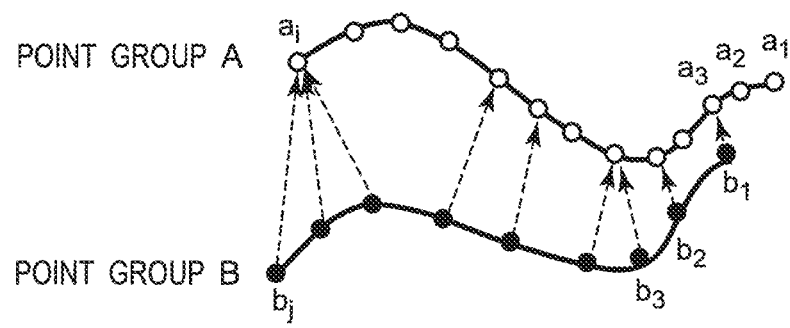
FIG. 13 is a schematic diagram illustrating the positioning method.

The distance between the point $a_i$ included in the point group A and the point group B is defined as a distance to the closest point included in the point group B (see (Mathematical formula 3) and FIG. 13), and a distance $d(a_i, B)$ between each point $a_i$ included in the point group A and the point group B is obtained.

$$d(a_i, B) = \min_{j \in 1\ldots M} d(a_i, b_j) \quad \text{[Mathematical formula 3]}$$
$$= d(a_i, m_i)$$

Assuming that $m_i \in B$ is a point corresponding to the point $a_i$, the rotation matrix R and the translation vector t that are the rigid body conversion parameters can be obtained by minimizing an error function E(R,t) indicated in the following equation (Mathematical formula 4).

$$E(R, t) = \sum_{i=1}^{N} |Ra_i + t - m_i| \quad \text{[Mathematical formula 4]}$$

In summary, the positioning rigid body conversion parameter can be obtained through the following procedure.

(i) In the points $a_i$ of the point group A, a closest point $m_i$ to the point group B is obtained.

(ii) The rigid body conversion parameter minimizing an error E is obtained.

(iii) The point group A is converted using the obtained parameter (R,t).

(iv) The repetitive calculation is ended when the error E is less than or equal to a threshold. Otherwise, the procedure returns to (i) to repeatedly perform the similar steps.

In implementing the present invention, the method for deciding the rigid body conversion parameter is described only by way of example. Alternatively, the point having the minimum distance can be set to the point at which the approximate calculation is started, and the error calculation method given by (Mathematical formula 4) can be converted into another method. Any method may be adopted as long as a matching degree of the rigid body position posture (freedom degree of 6) in the three-dimensional space, namely, magnitude of the error can numerically be evaluated. The same holds true for the following description.

Figure 3:
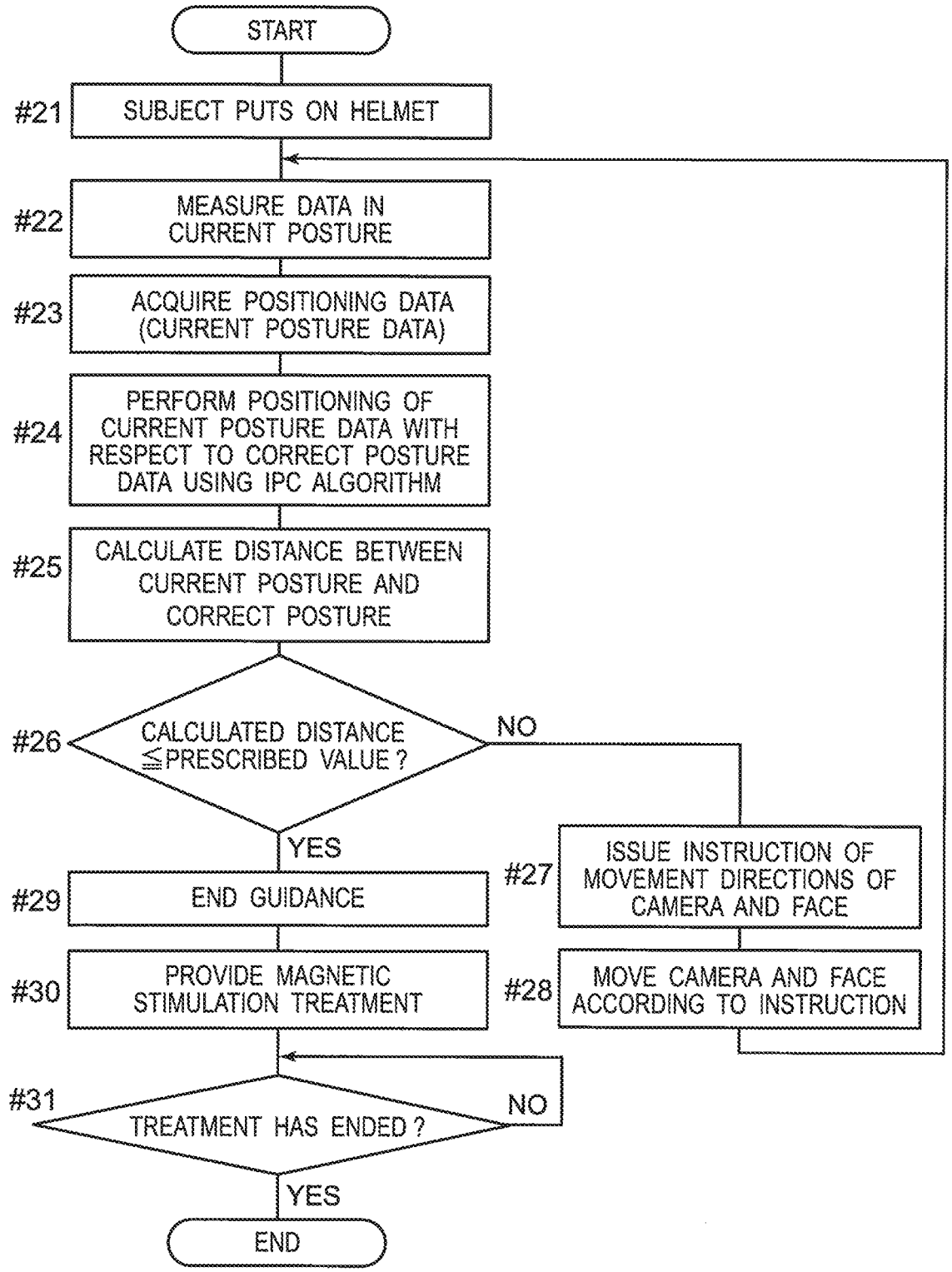
FIG. 3 is a flowchart illustrating a flow of the magnetic stimulation treatment performed with the device in FIG. 1.

The magnetic stimulation treatment performed with the transcranial magnetic stimulation device 1 of this embodiment will be described with reference to a flowchart in FIG. 3. The magnetic stimulation treatment can be provided as home treatment performed by the subject 2 or the family of the subject 2. During the home treatment, it is assumed that the positioning data in the "correct posture", which is obtained in the process of the flowchart in FIG. 2, is readably stored in the teaching information controller 23 of the transcranial magnetic stimulation device 1, the memory device provided in the teaching information controller 23, or the memory device provided outside the device body unit 20.

When the activation of the system is started, the subject 2 puts on the helmet 50 in Step #21, and the face shape data is measured in the mounting state (that is, in the "current posture") in Step #22. The measurement of the face shape data in the "current posture" is performed similarly to the measurement of the face shape data in the "correct posture", which is performed in Step #14 of FIG. 2. That is, the noise removing processing is performed on the surface shape data (point cloud data) measured with the TOF camera by the masking in which the distance information and the reliability information about the camera sensitivity are used and the data time average, thereby extracting only the face shape data.

Figure 7:
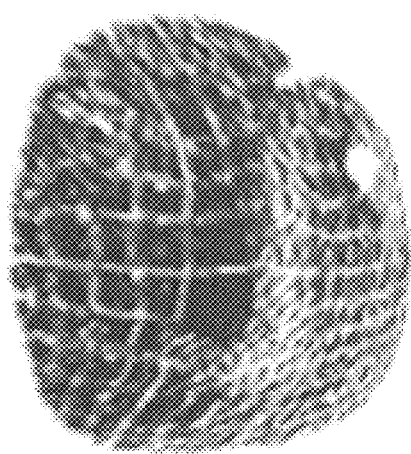
FIG. 7 is a view illustrating an example of the positioning data in a "current posture".

The positioning data is acquired for the purpose of the positioning with respect to the "correct posture" based on the measured face shape data in the "current posture" (Step #23). The acquisition of the positioning data in the "current posture" is performed similarly to the acquisition of the positioning data in the "correct posture", which is performed in Step #15 of FIG. 2. That is, only the shape data of the nose area that is the feature region is extracted from the face shape data obtained in Step #22, and the extracted shape data of the nose area is acquired as the positioning data in the "current posture". FIG. 7 illustrates an example of the positioning data in the "current posture".

Using the ICP algorithm, the positioning of the positioning data in the "correct posture", which is read from the teaching information controller 23, the memory device provided in the teaching information controller 23, or the memory device provided outside the device body unit 20, is performed with respect to the positioning data in the "current posture" (Step #24). The distance between the "correct posture" and the "current posture" is calculated (Step #25), and whether the calculated distance is less than or equal to a prescribed value is determined (Step #26). When the calculated distance exceeds the prescribed value (NO in Step #26), the instruction of the direction to be changed is issued on the monitor screen 12 of the image monitor 10, without performing the magnetic stimulation treatment, with respect to the relative relationship between the TOF camera 40 and the face of the subject 2 in the position and direction (Step #27).

As described above, the red circle C1 indicating the position of the TOF camera 40 in the current posture when viewed from one point decided in the head 2h of the subject 2 and the green circle C2 indicating the position of the TOF camera 40 in the correct posture when viewed from the same point decided in the head 2h of the subject 2 are displayed on the monitor screen 12 as an index indicating how much distance and in which direction the TOF camera 40 and the face of the subject 2 deviate from the "correct posture" (see FIG. 10).

The orientation of the line segment L12 connecting the two indexes C1 and C2 indicates the movement direction in which the relative positions of the TOF camera 40 and the face of the subject 2 should be moved such that the "current posture" is brought close to the "correct posture", and a length of the line segment L12 indicates the movement distance in which the relative positions of the TOF camera 40 and the face of the subject 2 should be moved.

The two indexes C1 and C2 are displayed by the circles because they represent the positions of the TOF camera 40 in the three-dimensional space. When the TOF camera 40 is close to the head 2h of the subject 2, the circles of the indexes C1 and C2 are largely displayed. When the TOF camera 40 (or the helmet 50 to which the TOF camera 40 is integrally fixed) is adjusted in a front-back direction depending on the positioning situation, the two indexes C1 and C2 become the same size, and the position of the TOF camera in the "current posture" can be matched with the position of the TOF camera 40 in the "correct posture" as the three-dimensional position.

As to the specific positioning operation, the head 2h of the subject 2 is stopped at the current position, the index C2 is moved, and the TOF camera 40 (that is, the helmet 50) is moved such that index C2 overlap with the index C1 and have the same size.

Alternatively, the helmet 50 integral with the TOF camera 40 is stopped at the current position, and the index C1 may be brought close to the index C2 when the face (head) of the subject 2 is moved. In this manner, similar positioning operation is performed.

In the case where the face of the subject 2 is moved so as to be brought close to the "correct posture", because the red circle C1 moves in the display screen according to the movement of the face, a person performing the operation such as the subject 2 moves the face such that the red circle C1 moves on the line segment L12 to be brought close to the green circle C2.

Alternatively, in the case where the TOF camera 40 is moved so as to be brought close to the "correct posture", because the red circle C1 similarly moves in the display screen according to the movement of the TOF camera 40, the person performs the operation such that the red circle C1 similarly moves on the line segment L12 to be brought close to the green circle C2. Alternatively, these operations may be simultaneously performed.

In this embodiment, the green circle C2 corresponding to the "correct posture" is displayed in the center of the display screen 12. On the other hand, the position and size of the red circle C1 corresponding to the "current posture" are changed in the monitor screen 12 by performing the operation to change the position and direction of the TOF camera 40 seen from the subject 2, and the circles C1 and C2 are displayed in the center of the monitor screen 12 when the "current posture" is matched with the "correct posture". Therefore, in the manner (mode) to display the circle C1, the display position and display size are changed in the monitor screen 12 by changing the current relative positions and directions of the TOF camera 40 and face.

Further, when the "current posture" is brought close to the "correct posture" according to the movement operation, the display position and display size in the screen 12 that are the display modes of the circle C1 are brought close to those of the circle C2.

The present invention is not limited to the above-described embodiment, but various modes can be made. For example, when the "current posture" is brought close to the "correct posture", the display color or shape of the index C1 may be close to those of the index C2. The operation teaching is not limited to the screen display, but may be performed by other transmission means such as a voice.

The term "movement" includes the operation to change the relative positions and directions of the face of the subject 2 and the TOF camera 40, namely, the position movement and the rotation operation of one of or both the face of the subject 2 and the TOF camera 40.

Thus, the subject 2 or the family of the subject 2 changes the relative relationship (that is, the mounting condition of the helmet 50) between the TOF camera 40 and the face of the subject 2 in the position and direction such that the line segment L12 in the monitor screen 12 is shortened and such that the two circles C1 and C2 finally overlap each other.

In the above-described embodiment, the circles C1 and C2 that are the indexes finally overlap with each other such that the "current posture" becomes the "correct posture". Alternatively, the "correct posture" may be displayed by a certain specific positional relationship without making the circles C1 and C2 overlap each other.

According to the instruction on the monitor screen 12, the subject 2 or the family of the subject 2 adjusts the mounting condition of the helmet 50, and changes the relative relationship between the TOF camera 40 and the face of the subject 2 in the position and direction (Step #28). Then, the flow returns to Step #22 to measure the data in the "current posture" again. Steps #22 to #26 are repeatedly performed until the distance between the "correct posture" and the "current posture" becomes the prescribed value or less (YES in Step #26), which allows the magnetic stimulation coil 30 to be guided to the correct position.

Figure 11:
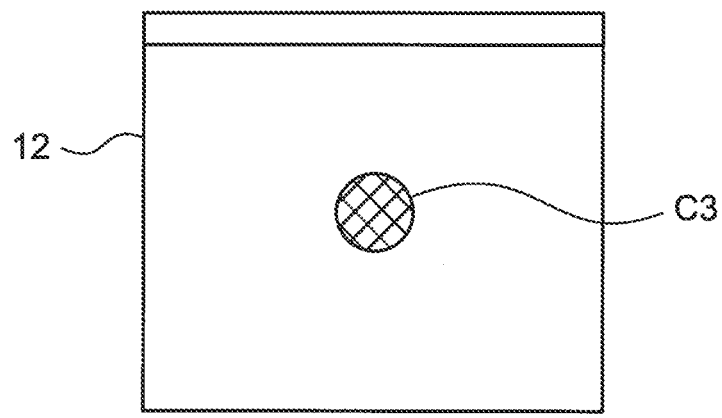
FIG. 11 is a view illustrating an example of the teaching information displayed on the image monitor.

When the distance between the "correct posture" and the "current posture" becomes the prescribed value or less (YES in Step #26) to guide the magnetic stimulation coil 30 to the correct position, a single yellow circle C3 indicating the end of the guidance process is displayed on the monitor screen 12 of the image monitor 10 as illustrated in FIG. 11, and the guidance process is ended (Step #29).

The magnetic stimulation treatment is provided in the state where the magnetic stimulation coil 30 is guided to the correct position and direction in this manner (Step #30). That is, the subject 2 or the family of the subject 2 activates the magnetic stimulation coil controller 22 so that the magnetic flux having the predetermined intensity is applied from the magnetic stimulation coil 30 to generate the induction current in the head 2h of the subject 2, and the magnetic stimulation is applied to the optimum stimulation region.

The transcranial magnetic treatment device 1 of the embodiment of the present invention performs the above operation teaching, which allows the operator to intuitively know which direction to move the movement operation object such as the face of the subject 2 or the TOF camera 40 from the display screen 12. Therefore, the operation is facilitated, the obstacle is reduced when the transcranial magnetic stimulation device 1 is used at home or the medical practitioner outpatient, and the transcranial magnetic stimulation device 1 is expected to become widespread.

The plurality of operation objects such as the face of the subject 2 and the TOF camera 40 are provided, one of the face and the TOF camera 40 or both the face and the TOF camera 40 can be selected according to conditions such as the disease condition of the subject 2, namely, how exercise capacities of arms and legs are lowered from an aftereffect of an apoplexy, whether the subject 2 is right-handed or left-handed, and whether a helper exists. Therefore, a large freedom degree is generated in the operability, and the obstacle in use of the treatment device is also reduced to promote the spread of the device.

The magnetic stimulation treatment is continuously performed until a predetermined treatment effect is obtained (or predetermined time elapses) to end the magnetic stimulation treatment (NO in Step #31), and the activation of the device 1 is stopped when the magnetic stimulation treatment is ended (YES in Step #31).

As described above, in the transcranial magnetic stimulation device 1 of this embodiment, the use of the TOF camera 40 can obtain the three-dimensional shape information about the subject's head 2h in real time. In this case, because the TOF camera 40 and the magnetic stimulation coil 30 are integrally movable and/or rotatable, the relative relationship between the TOF camera 40 and the magnetic stimulation coil 30 is always constant with respect to the position and direction, and it is not necessary to adjust the position and direction again. The feature region (for example, the nose area) of the face shape is extracted from the three-dimensional shape information about the subject's head 2h to obtain the pieces of positioning data in the "correct posture" and the "current posture", the deviation between the "correct posture" and the "current posture" is calculated based on the pieces of positioning data, and the teaching information can be generated in order to perform the operation to change the relative positions and directions of the magnetic stimulation coil 30 and the subject's head 2h, and displayed on the monitor screen 12 of the image monitor 10.

Accordingly, even if the magnetic stimulation coil 30 deviates from the relative position and direction corresponding to the specific region in the subject's head 2h because of the deviation of the mounting posture of the helmet 50 when the relative movement and/or rotation operation between the magnetic stimulation coil 30 and the subject's head 2h is performed in order to guide the magnetic stimulation coil 30 located outside the head to the position and direction corresponding to the specific region of the subject's head 2h, the magnetic stimulation coil 30 can be easily and reliably adjusted to the relative position and direction corresponding to the specific region of the subject's head 2h only by the simple operation to adjust the mounting posture of the helmet 50 to relatively move and/or rotate the magnetic stimulation coil 30 and the subject's head 2h according to the display information on the monitor screen 12. Therefore, the burden on the subject 2 caused by the head restriction can be reduced during the transcranial magnetic stimulation therapy. The feature region of the face shape is extracted from the three-dimensional shape information about the subject's head 2h to calculate the deviation of the three-dimensional shape information, so that the information for the operation teaching can be obtained at a relatively high speed.

As described above, the user of the device 1 can perform the necessary operation without any conventional special skill only by adjusting the mounting posture of the helmet 50 to relatively move and/or rotate the magnetic stimulation coil 30 and the subject's head 2h according to the information for the operation teaching displayed on the monitor screen 12. Even the subject 2, the family of the subject 2, or the nearby family doctor who is not always the expert can relatively easily operate and use the device 1. Because the conventional large-scale, expensive device is not required, cost can be reduced, and an installation space can easily be ensured in the subject's home or in the relatively small doctor's office and clinic. As described above, the present invention can provide the compact and inexpensive transcranial magnetic stimulation device 1 in which the handling and operation are simplified, which allows the subject 2 to consecutively and repeatedly receive the transcranial magnetic stimulation therapy every day at home or at the nearby family doctor's office.

Figure 14:
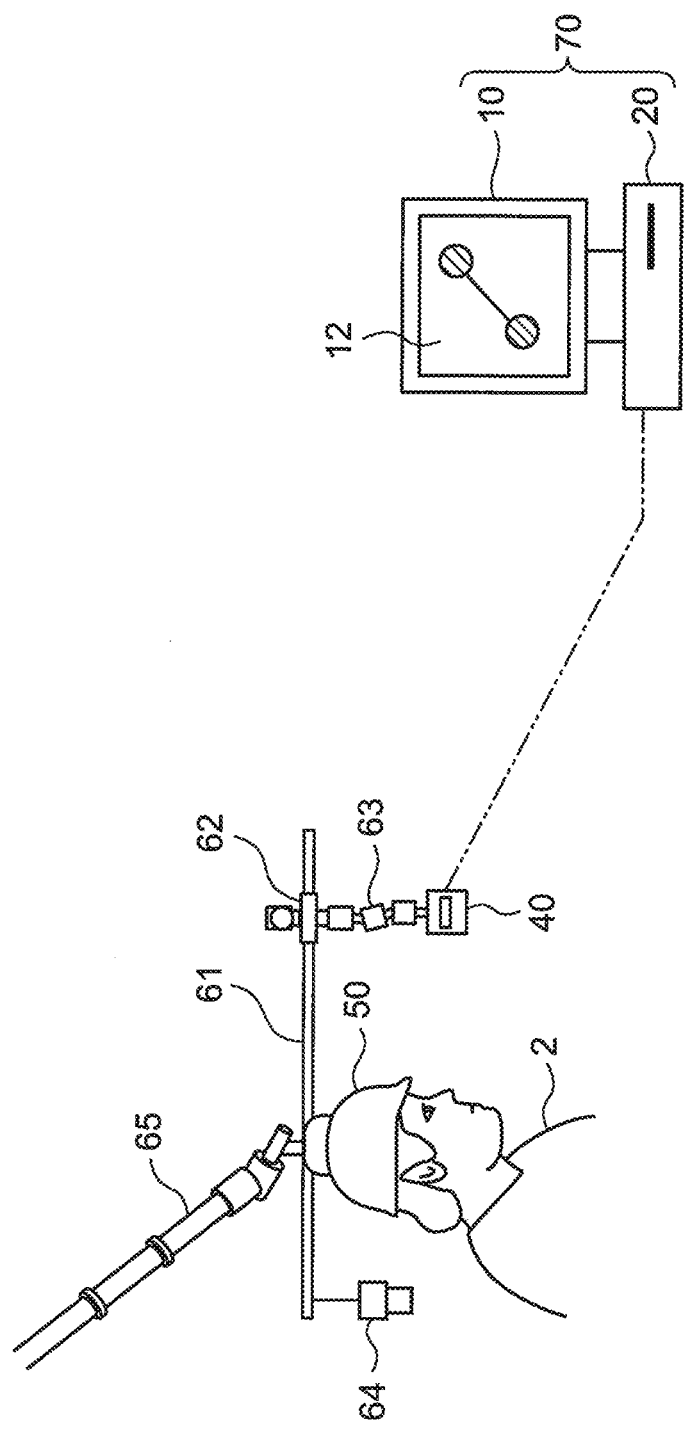
FIG. 14 is a schematic configuration diagram illustrating an experimental device used in accuracy evaluation for the device in FIG. 1.
Figure 15:
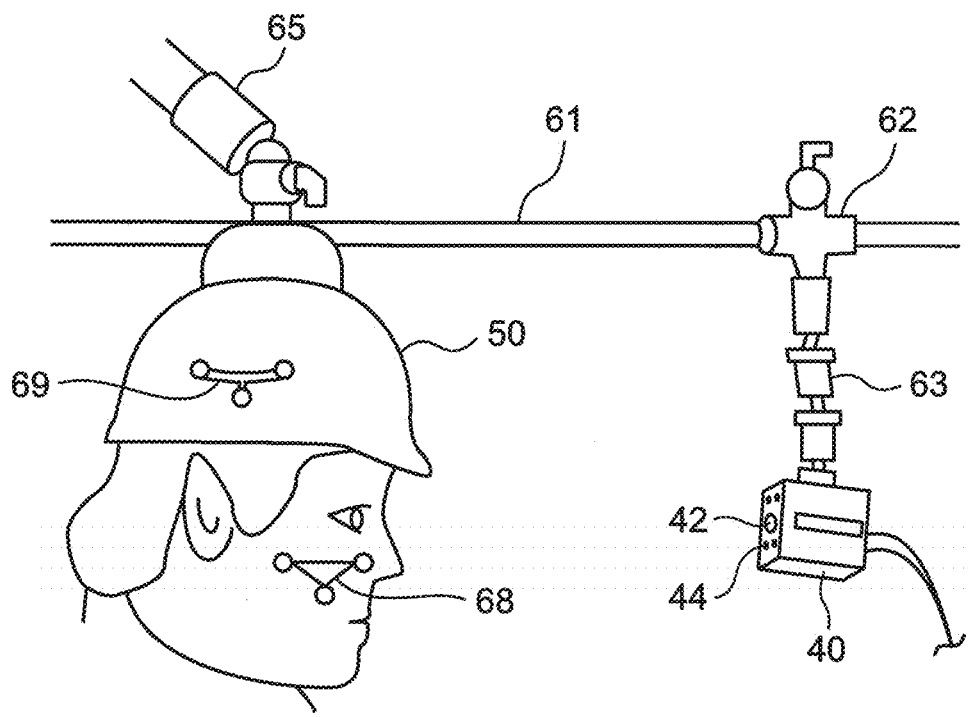
FIG. 15 is an enlarged view of a part of FIG. 14.

An experiment was performed to check adjustment accuracy of the position and direction between the subject 2 and the helmet 50 in order to check guidance accuracy of the magnetic stimulation coil 30 in the transcranial magnetic stimulation device 1 of this embodiment. FIG. 14 is a schematic configuration diagram illustrating an experimental device used in accuracy evaluation. FIG. 15 is an enlarged view of a part of FIG. 14.

As illustrated in FIGS. 14 and 15, in this experiment, a holding rod 61 is fixed to a top of the helmet 50 while being upright, and the fixed portion is connected to a terminal portion of an arm support member 65. That is, the helmet 50 and the holding rod 61 are wholly supported by the arm support member 65. The TOF camera 40 is attached to one side (a front side of the subject 2) of the holding rod 61 via a joint 62 and a multi-joint type holding arm 63. The joint 62 and the holding arm 63 are slidably adjustable along the rod 61. That is, the TOF camera 40 is integrally fixed to the helmet 50 via the holding arm 63, the joint 62, and the holding rod 61. A weight (balancer) 64 is attached to the other side (a rear side of the subject 2) of the holding rod 61 in order to keep balance with a weight of the TOF camera 40.

In this experiment, Swiss Ranger SR4000 (product of MESA in Switzerland) was used as the TOF camera 40. The TOF camera 40 includes a light receiver 42 in the center of a front surface thereof, and a plurality of light emitters 44 are provided around the light receiver 42. The TOF camera 40 used in the device 1 of FIG. 1 has the similar configuration.

For convenience, in the description of the configuration of the device 1, the image monitor 10 and the device body unit 20 are separately illustrated in FIG. 1. However, in actual, as illustrated in FIG. 14, the image monitor 10 and the device body unit 20 are preferably integrally provided to constitute a so-called personal computer (PC) 70. Therefore, the compact transcranial magnetic stimulation device 1 is obtained, the installation space is reduced, and the transcranial magnetic stimulation device 1 is more suitably used at home. The TOF camera 40 is connected to the device body unit 20 of the personal computer 70 so as to be able to receive and transmit a signal.

In this experiment, Polaris Vicra (product of NDI) was used to correctly measure the relative relationship between the subject 2 and the helmet 50 in the position and posture. The polaris system is a high-performance optical 3D measurement system, and the three-dimensional position of an infrared reflection marker can accurately be measured. As illustrated in FIG. 15, polaris markers 68 and 69 are adhered to the subject 2 and the helmet 50, and the guidance accuracy was checked from the relative relationship between the two markers 68 and 69 in the position and direction.

In this experiment, the helmet 50 is put on the subject 2, and the "correct posture" is set. In the "correct posture", the nose area shape of the subject 2 is measured with the TOF camera 40, and the relative relationship between the polaris markers 68 and 69 in the position and direction is measured with Polaris Vicra. Then, the subject 2 puts on the helmet 50 again, and the similar measurement is performed on the "current posture". The face of the subject 2 and the camera are moved until the "current posture" is matched with the "correct posture", and when the "current posture" is matched with the "correct posture" to end the guidance, the positional relationship between the markers at the end of the guidance is measured with Polaris Vicra. Such a trial was repeated ten times to measure change angles of the distance between the two polaris markers 68 and 69 and the direction, and the accuracy was evaluated based on the measured data by determining whether the mounting posture of the helmet 50 on the subject 2 at the end of the guidance fell within a target range compared with the "correct posture".

It is assumed that effective accuracy in performing the magnetic stimulation treatment is a diameter of about 6 mm in the cranial, and that the posture change angle in providing the magnetic stimulation is about 5 degrees. Therefore, the target accuracy of the distance error was set to 6 mm or less, and the target accuracy of the angle error was set to 5 degrees or less.

Figure 16:
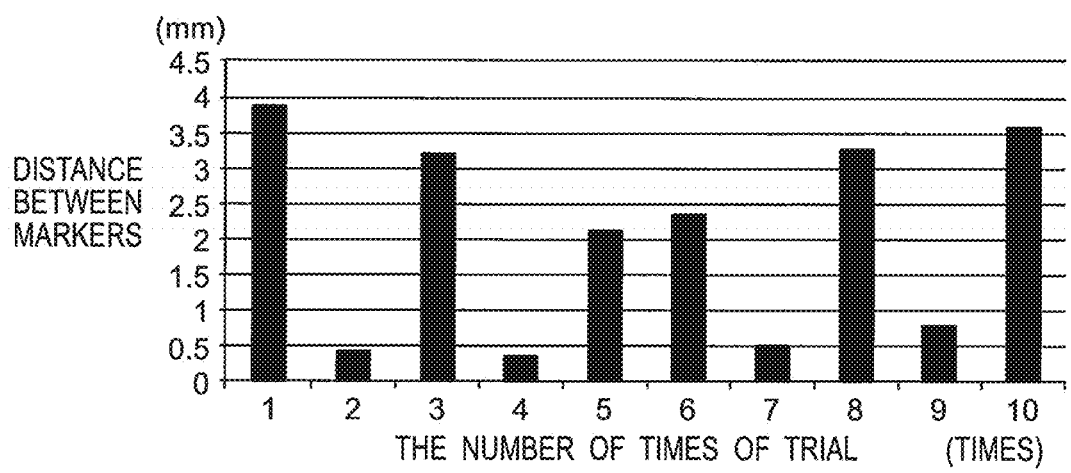
FIG. 16 is a view illustrating an accuracy evaluation result in which the experimental device is used.
Figure 17:
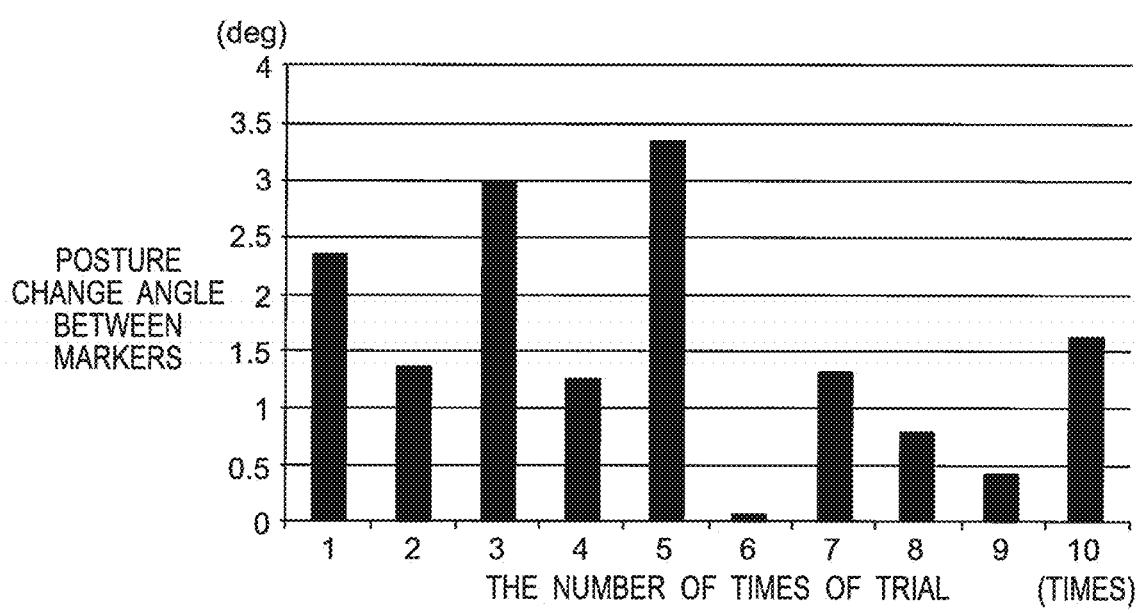
FIG. 17 is a view illustrating the accuracy evaluation result.

Experimental results are illustrated in FIG. 16 (distance between markers) and FIG. 17 (posture change angle between markers). As can be seen from a graph in FIG. 16, in all the trials, both the distance error and the angle error fall within the target accuracy (diameter of 6 mm and 5 degrees). The average distance error was 1.54 mm, and a standard deviation was 1.40. The average angle error was 2.04 degrees, and the standard deviation was 1.02 degrees.

According to the experimental results, the distance error and the angle error satisfied the target accuracy in all the trials, and good results were obtained with respect to the average value and the standard deviation. Therefore, it is confirmed that this system satisfies the accuracy required for the magnetic stimulation treatment.

In the above description, the device is used in the transcranial magnetic stimulation therapy in which the magnetic stimulation is applied to the intracerebral nerve of the subject with the magnetic stimulation coil to relieve the neuropathic pain. The present invention is not limited to the transcranial magnetic stimulation therapy, and the present invention can effectively be applied to other magnetic stimulation applications.

The present invention is not limited to the above embodiment, but various changes and design improvements can be made without departing from the gist of the present invention.

INDUSTRIAL APPLICABILITY

The present invention can be effectively used as the operation teaching device in which handling and operation are simplified while the burden on the patient caused by the head restriction is reduced during the transcranial magnetic stimulation therapy, and the transcranial magnetic stimulation device in which the operation teaching device is used.

DESCRIPTION OF REFERENCE SYMBOLS

1 TRANSCRANIAL MAGNETIC STIMULATION DEVICE
2 SUBJECT
2h SUBJECT'S HEAD
10 IMAGE MONITOR
12 MONITOR SCREEN
20 DEVICE BODY UNIT
21 IMAGE DISPLAY CONTROLLER
22 MAGNETIC STIMULATION COIL CONTROLLER
23 TEACHING INFORMATION GENERATOR
30 MAGNETIC STIMULATION COIL
40 TOF CAMERA
42 LIGHT RECEIVER
44 LIGHT EMITTER
50 HELMET
68, 69 POLARIS MARKER
70 PERSONAL COMPUTER

The invention claimed is:

1. An operation teaching device used in operation teaching during movement and/or rotation operation of an object in order to adjust the object to a predetermined position and direction, the operation teaching device comprising:
 time-of-flight (TOF) depth image camera configured to obtain three-dimensional shape information about the object from information about a propagation distance of projection light from light emitter to light receiver through reflection on the object in each pixel of a photographed image obtained by irradiating a surface of the object with the projection light;
 wherein the operation teaching device is configured to:
  extract a feature region from the three-dimensional shape information using a luminance image of the object obtained from information about light receiving intensity of the projection light, the projection light being reflected from the object and received with the light receiver; and
  generate information for the operation teaching by calculating a deviation between the three-dimensional shape information including the feature region of the object in the predetermined position and direction and the three-dimensional shape information including the feature region of the object in a current position and direction;
 wherein the operation teaching device is configured to display on a screen:
  a first index indicating a position of the TOF depth image camera when viewed from one point of the object in the current position;
  a second index indicating a position of the TOF depth image camera when viewed from the one point of the object in a predetermined position; and
  a line segment connecting between the first index and the second index, and
 wherein an orientation of the line segment indicates a movement direction in which the TOF depth image camera or the object is to be moved such that the current position is brought closer to the predetermined position, and a length of the line segment varies depending upon the deviation.

2. The operation teaching device as claimed in claim 1, wherein the TOF depth image camera is fixed to the object such that a change in position of the object results in a corresponding change in position of the TOF depth image camera.

3. An operation teaching device comprising:
 time-of-flight (TOF) depth image camera configured to enable movement and/or rotation operation of an object and to obtain three-dimensional shape information about the object from information about a propagation distance of projection light from light emitter to light receiver through reflection on the object in each pixel of a photographed image obtained by irradiating a surface of the object with the projection light;

wherein the operation teaching device is configured to:
generate, based on (A) the three-dimensional shape information about the object located in a predetermined position and direction relative to the depth image camera and (B) the three-dimensional shape information about the object located in a current position and direction relative to the depth image camera:
(1) a first index indicating predetermined relative position and direction, and
(2) a second index indicating the current relative position and direction, a display mode of the second index being brought close to a display mode of the first index when operation to relatively move one of the object and the depth image camera is performed such that one of the object and the depth image camera is brought close to the predetermined relative position and direction;

wherein the operation teaching device is configured to display on a screen:
the first index;
the second index; and
a line segment connecting between the first index and the second index, and wherein an orientation of the line segment indicates a movement direction in which the TOF depth image camera or the object is to be moved such that the current position is brought closer to the predetermined position, and a length of the line segment varies depending upon the a deviation between the (A) the three-dimensional shape information about the object located in the predetermined position and direction relative to the depth image camera and (B) the three dimensional shape information about the object located in the current position and direction relative to the depth image camera.

4. The operation teaching device as claimed in claim 3, wherein the TOF depth image camera is fixed to the object such that a change in position of the object results in a corresponding change in position of the TOF depth image camera.

5. A transcranial magnetic stimulation device for applying magnetic stimulation to a specific region in a subject's head using magnetic field generator located outside the head, the transcranial magnetic stimulation device comprising:
time-of-flight (TOF) depth image camera that is provided to be movably and/or rotatably integral with the magnetic field generator, the TOF depth image camera being configured to obtain three-dimensional shape information about the subject's head from information about a propagation distance of projection light from light emitter to light receiver through reflection on a surface of the subject's head in each pixel of a photographed image obtained by irradiating a surface of the subject's head with the projection light;

wherein the transcranial magnetic stimulation device is configured to:
extract a feature region from the three-dimensional shape information using a luminance image of the subject's head obtained from information about light receiving intensity of the projection light, the projection light being reflected from the surface of the subject's head and received with the light receiver; and generate teaching information for operation to change relative positions and directions of the magnetic field generator and the subject's head by calculating a deviation between the three-dimensional shape information including the feature region of the subject's head in a position and direction in which the magnetic stimulation is provided to the specific region and the three-dimensional shape information including the feature region of the subject's head in a current position and direction;

wherein the operation teaching device is configured to display on a screen:
a first index indicating a position of the TOF depth image camera when viewed from one point of the subject's head in the current position,
a second index indicating a position of the TOF depth image camera when viewed from the one point of the subject's head in a predetermined position; and
a line segment connecting between the first index and the second index; and wherein an orientation of the line segment indicates a movement direction in which the TOF depth image camera or the subject's head is to be moved such that the current position is brought closer to the predetermined position, and a length of the line segment varies depending upon the deviation.

6. The transcranial magnetic stimulation device as claimed in claim 5, wherein the feature region is a nose area of the subject.

7. The transcranial magnetic stimulation device as claimed in claim 5, wherein the feature region is an ear area of the subject.

8. The transcranial magnetic stimulation device as claimed in claim 5,
wherein the TOF depth image camera is fixed to the subject's head such that a change in position of the subject's head results in a corresponding change in position of the TOF depth image camera.

9. A transcranial magnetic stimulation device for applying magnetic stimulation to a specific region in a subject's head using magnetic field generator located outside the head, the transcranial magnetic stimulation device comprising:
time-of-flight (TOF) depth image camera provided to be movably and/or rotatably integral with the magnetic field generator to obtain three-dimensional shape information about the subject's head from information about a propagation distance of projection light from light emitter to light receiver through reflection on a surface of the subject's head in each pixel of a photographed image obtained by irradiating a surface of the subject's head with the projection light;

wherein the transcranial magnetic stimulation device is configured to:
generate, based on (A) the three-dimensional shape information about the subject's head when the magnetic field generator is located in a position and direction in which the magnetic stimulation is provided to the specific region and (B) the three-dimensional shape information about the subject's head when the magnetic field generator is located in a current position and direction:
(1) a first index indicating a target position and direction when the magnetic field generator provides the magnetic stimulation to the specific region, and
(2) a second index indicating the current position and direction when the magnetic field generator is located in the current position and direction, a display mode of the second index being brought close to a display mode of the first index when operation to move the magnetic field generator is performed such that the magnetic field generator is brought close to the position and direction in which the magnetic stimulation is provided to the specific region;

wherein the operation teaching device is configured to display on a screen:
 the first index;
 the second index; and
 a line segment connecting between the first index and the second index; and wherein an orientation of the line segment indicates a movement direction in which the TOF depth image camera or the subject's head is to be moved such that the current position is brought closer to the predetermined position, and a length of the line segment varies depending upon the a deviation between the (A) the three-dimensional shape information about the subject's head located in the predetermined position and direction relative to the depth image camera and (B) the three dimensional shape information about the subject's head located in the current position and direction relative to the depth image camera.

10. The transcranial magnetic stimulation device as claimed in claim 9,
 wherein the TOF depth image camera is fixed to the subject's head such that a change in position of the subject's head results in a corresponding change in position of the TOF depth image camera.

* * * * *